United States Patent [19]

Steiner et al.

[11] 4,336,192

[45] Jun. 22, 1982

[54] 5,6-DIHYDRO-11-ALKYLENE-MORPHAN-THRIDIN-6-ONES

[75] Inventors: Gerd Steiner, Kirchheim; Albrecht Franke, Wachenheim, both of Fed. Rep. of Germany

[73] Assignee: BASF Aktiengesellschaft, Fed. Rep. of Germany

[21] Appl. No.: 208,974

[22] Filed: Nov. 20, 1980

Related U.S. Application Data

[63] Continuation of Ser. No. 144,061, Apr. 28, 1980, abandoned.

[30] Foreign Application Priority Data

May 10, 1979 [DE] Fed. Rep. of Germany ....... 2918832

[51] Int. Cl.$^3$ ............................................. C07D 223/20
[52] U.S. Cl. ..................... 260/239.3 T; 260/239 D; 546/200; 544/359; 424/244; 424/267; 424/250
[58] Field of Search .................................. 260/239.3 T

[56] References Cited

U.S. PATENT DOCUMENTS

| | | | |
|---|---|---|---|
| 3,391,136 | 7/1968 | Berg | 260/239.3 T |
| 3,431,257 | 3/1969 | Aichingeg et al. | 260/239.3 T |
| 3,580,907 | 5/1971 | Thiel et al. | 260/239.3 T |

FOREIGN PATENT DOCUMENTS

| | | | |
|---|---|---|---|
| 1568217 | 1/1970 | Fed. Rep. of Germany | 260/239.3 T |
| 1144829 | 3/1969 | United Kingdom | 260/239.3 T |

OTHER PUBLICATIONS

March, "Advanced Organg Chemistry", (McGraw-Hill), 1968, pp. 202–209.
Hunziker et al., "Helv. Chim. Acta", 49, (1966), pp. 1433–1439.
Caronna, "Gazzetta Chimica Italiana", (1954), vol. 84, pp. 1133–1140.
Hardtmann et al., "J. Organic Chemistry", (1969), vol. 34, pp. 2244–2248.

*Primary Examiner*—Robert T. Bond
*Attorney, Agent, or Firm*—Keil & Witherspoon

[57] ABSTRACT

5,6-Dihydro-11-alkylene-morphanthridin-6-ones and processes for their preparation. The compounds are valuable intermediates for chemical syntheses, especially of drugs.

2 Claims, No Drawings

5,6-DIHYDRO-11-ALKYLENE-MORPHANTHRIDIN-6-ONES

This is a continuation of application Ser. No. 144,061, filed Apr. 28, 1980, now abandoned.

The present invention relates to 5,6-dihydro-11-alkylene-morphanthridin-6-ones of the general formula I

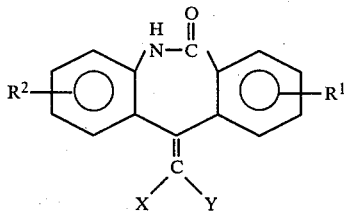

where $R^1$ and $R^2$ are hydrogen, fluorine, chlorine, methyl or trifluoromethyl, X is hydrogen or methyl and Y is cyano, methylcarbonyl, carboxamide, which may or may not be substituted at the amide nitrogen by one or two lower alkyl of 1 to 3 carbon atoms, or alkoxycarbonyl, where alkoxy is of 1 to 3 carbon atoms, these compounds being valuable intermediates for chemical syntheses, especially of drugs.

It is to be noted that the novel compounds, of the formula I, exist as cis-trans isomers Ia and Ib.

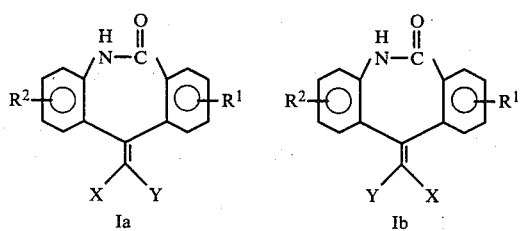

If required, the cis-trans isomers may be separated by conventional methods, for example by fractional crystallization or column chromatography. The configuration of the individual isomers can be established by, for example, X-ray analysis, as is shown in the Examples.

The compounds of the formula I are prepared by carbonyl-olefination, wherein a 5,6-dihydro-morphanthridine-6,11-dione of the formula II

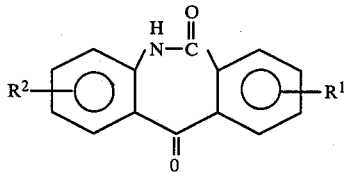

where $R^1$ and $R^2$ have the meanings given for formula I, is reacted with a phosphonate of the formula IIIa

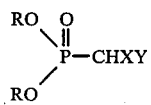

where R is alkyl of 1 to 3 carbon atoms and X and Y have the meanings given for formula I, under the conditions of a Wittig-Horner reaction, in an inert solvent (dimethylformamide being particularly preferred), in the presence of one mole equivalent of a base, preferably a sodium alcoholate, or sodium hydride or sodium amide, at from 20° to 80° C., or is reacted with a phosphonium salt of the formula IIIb

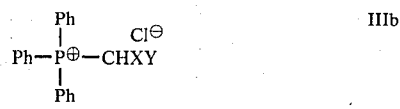

where Ph is phenyl and X and Y have the meanings given for formula IIIa, under the conditions of the conventional Wittig reaction, in an aprotic organic solvent, especially a saturated aliphatic or saturated cyclic ether, eg. diethyl ether, tetrahydrofuran or dioxane or, preferably, in dimethylformamide, in the presence of one mole equivalent of a base, especially of an alkali metal alcoholate, preferably sodium methylate or sodium ethylate, or sodium hydride or sodium amide, or an organometallic compound, eg. butyl-lithium, at from 20° to 100° C.

Surprisingly, the above reactions carried out on the substituted heterocyclic 7-membered ring lead smoothly to the novel compounds of the formula I.

A further possible method of preparation of novel compounds of the formula I, where Y is unsubstituted or substituted carboxamide is to hydrolyze the 5,6-dihydro-11-carbalkoxymethylene-morphanthridin-6-one of the formula I, where Y is —COOR, R being lower alkyl of 1 to 3 carbon atoms, with an alcoholic alkali metal hydroxide solution at from 40° to 90° C., in a conventional manner to the carboxylic acid, then to convert the resulting 5,6-dihydro-11-carboxymethylene-morphanthridin-6-one of the formula I, where Y is carboxyl, to the carboxylic acid chloride by reaction with thionyl chloride in an inert solvent at from 20° to 80° C., and thereafter to convert the acid chloride, by reaction with ammonia or an amine of the formula

where the R's are lower alkyl of 1 to 3 carbon atoms, advantageously in an aqueous medium or in an inert organic solvent, eg. a cyclic saturated ether, especially tetrahydrofuran or dioxane, advantageously at from 50° to 90° C., to the corresponding 5,6-dihydro-11-carboxamidomethylene-morphanthridin-6-one.

Some of the 5,6-dihydro-morphanthridine-6,11-diones of the formula II are known from the literature (F. Hunziker et al., Helv. Chim. Acta 49 (1966), 1433–1439; L. H. Werner et al., J. Med. Chem. 8 (1965), 74–80; G. Caronna et al., Gazz. chim. ital. 84 (1954), 1135–1140); where the compounds have not been previously described, they can be obtained from corresponding anthraquinones by enlarging the ring by a Schmidt reaction, as described in the Examples, or by halogen-substitution of the basic molecule (E. Hardtmann and H. Ott, J. Org. Chem. 34 (1969), 2244–2248).

The novel compounds of the formula I are valuable intermediates for the synthesis of pharmacologically active compounds.

Reaction of the compounds of the formula I, by a conventional method, with excess phosphorus oxychloride, which at the same time serves as the solvent, in the presence or absence of a catalytic amount of N,N-dimethylaniline, by refluxing for from 3 to 6 hours, gives the corresponding imino-chloride of the formula IV, which may be isolated by distilling off the excess phosphorus oxychloride and working up the residue in an aqueous two-phase system by extraction with a chlorohydrocarbon, eg. chloroform or methylene chloride.

The imino-chloride of the formula IV

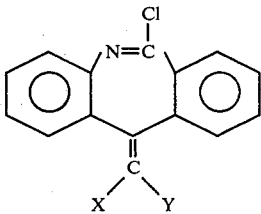

IV may be used to prepare compounds of the formula V

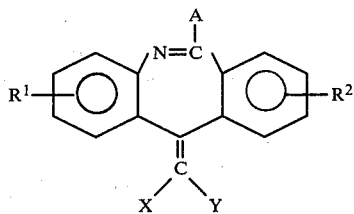

V where $R^1$, $R^2$, X and Y have the meanings given for formula I and A is $-OR^3$, where $R^3$ is aminoalkyl, alkyl being of 2 or 3 carbon atoms and the amine nitrogen being disubstituted by methyl or ethyl, or is N-methyl-piperidinomethyl, which may or may not be in the form of the N-oxide, or A is the amino radical

which is piperidine, piperazine or homopiperazine, which may or may not be substituted by methyl or hydroxyl at the ring carbon atoms and substituted at the additional ring nitrogen, where such is present, by methyl, ethyl, β-hydroxyethyl, cyclopropyl or propynyl, and may or may not be in the form of a N-oxide, or where one of $R^4$ and $R^5$ is hydrogen and the other is aminoalkyl, where alkyl is of 2 or 3 carbon atoms and the amine nitrogen is disubstituted by methyl or ethyl, or is N-methyl-piperidinomethyl, which may or may not be in the form of the N-oxide, by reaction with a nucleophilic agent AH, where A has the above meanings, advantageously in the presence of an excess amount of the amine or alcohol AH, which excess also serves as the solvent and may or may not serve as an acid-binding agent. The reaction may or may not be carried out in the presence of an inert solvent, eg. a cyclic saturated ether, especially tetrahydrofuran or dioxane, benzene or another benzene hydrocarbon, eg. xylene, mesitylene or decahydronaphthalene. The reaction is a rule carried out at from 80° to 150° C., preferably from 90° to 120° C., and is in general complete within from 3 to 10 hours. It is at times advantageous to exclude atmospheric oxygen and carry out the reaction under an inert gas, for example under nitrogen.

Advantageously, the nucleophilic agent AH is employed in the reactions in from 2-fold to 20-fold molar excess.

The free 6-substituted 11-alkylene-morphanthridines of the formula V may, if required, be converted in a conventional manner to the N-oxides and/or to addition salts with pharmacologically acceptable acids. Examples of such acids are hydrochloric acid, maleic acid and methanesulfonic acid.

The compounds of the formula V, their pure cis-trans isomers, and their addition salts with pharmacologically acceptable acids exhibit valuable pharmacological properties. By virtue of their pharmacodynamic characteristics, they may in particular be used as neuroleptics, sedatives, hypnotics, agents for treating Parkinson's syndrome, analgesics or antidepressants.

Drugs, containing conventional carriers or diluents and conventional technical auxiliaries, may be prepared in a conventional manner, in accordance with the desired route of administration, and in dosage units appropriate for the particular application. Suitable single doses for man are from 10 to 100 mg.

Examples of compounds of the formula V are: cis,-trans-11-cyanomethylene-6-(4-methyl-piperazin-1-yl)-morphanthridine; cis 11-cyanomethylene-6-(4-methyl-piperazin-1-yl)-morphanthridine; trans-11-cyanomethylene-6-(4-methyl-piperazin-1-yl)-morphanthridine; cis,-trans-11-cyanomethylene-6-(4-methyl-4-oxy-piperazin-1-yl)-morphanthridine; cis-11-cyanomethylene-6-(4-methyl-4-oxy-piperazin-1-yl)-morphanthridine; trans-11-cyanomethylene-6-(4-methyl-4-oxy-piperazin-1-yl)-morphanthridine; cis,trans-11-cyanomethylene-2-methyl-6-(4-methyl-piperazin-1-yl)-morphanthridine; cis,-trans-11-cyanomethylene-3-methyl-6-(4-methyl-piperazin-1-yl)-morphanthridine; cis,trans-11-cyanomethylene-6-(4-ethyl-piperazin-1-yl)-morphanthridine; cis,-trans-11-cyanomethylene-6-(2-piperidin-1-yl-ethylamino)-morphanthridine; cis,trans-11-cyanomethylene-6-(N-methyl-piperidin-3-yl-methoxy)-morphanthridine and cis,trans-11-cyanomethylene-6-(N'-methyl-homopiperazin-1-yl)-morphanthridine.

The Examples which follow illustrate the invention.

I. Preparation of compounds according to the invention:

EXAMPLE 1 cis,trans-11-Cyanomethylene-5,6-dihydro-morphanthridin-6-one (a) 30.0 g (135 millimoles) of 5,6-dihydro-morphanthridine-6,11-dione are dissolved in 300 ml of dimethylformamide and the solution is stirred under nitrogen. 35.4 g (200 millimoles) of diethyl cyanomethyl-phosphonate and 35.0 g (200 millimoles) of sodium methylate solution (30% strength) dissolved in 100 ml of dimethylformamide are then slowly added dropwise at the same time. An increase in the depth of color, and a rise in temperature, indicate that the Wittig reaction has started. After stirring the mixture for a further 12 hours at room temperature, the reaction product is poured into ice water and the solid which has precipitated is filtered off. The crude product is thoroughly washed with water, dried and recrystallized from ethanol. Yield: 32.5 g (98%) of 11-cyanomethylene-5,6-dihydro-morphanthridin-6-one, in the form of colorless crystals of melting point 221°–223° C.

(b) Conventional Wittig process: triphenyl-cyanomethyl-phosphonium chloride is introduced into dimethylformamide, 1 mole equivalent of a 30% strength sodium methylate solution is then added dropwise, or 1 mole equivalent of sodium hydride is added, and finally 1 mole equivalent of a solution of 5,6-dihydro-morphanthridine-6,11-dione in dimethylformamide is also introduced. The reaction mixture is then stirred for from 5 to 8 hours at 50°–80° C., then poured into ice water, and extracted repeatedly with methylene chloride. The organic phase is dried, the solvent is removed, and the crude product is recrystallized from ethanol. Yield: 67% of colorless crystals of melting point 220°–222° C.

EXAMPLE 2 cis,trans-11-Carbomethoxymethylene-5,6-dihydro-morphanthridin-6-one cis,trans-11-Carbomethyoxymethylene-5,6-dihydro-morphanthridin-6-one is prepared by the method of Example 1a from 5,6-dihydro-morphanthridine-6,11-dione and diethyl carbomethoxymethyl-phosphonate as the Wittig-Horner reagent. Yield 96%, melting point 184°–185° C.

EXAMPLE 3 cis,trans-11-Carboxamidomethylene-5,6-dihydro-morphanthridin-6-one (a) cis,trans-11-Carboxamidomethylene-5,6-dihydro-morphanthridin-6-one is prepared by the method of Example 1a, using diethyl-phosphonoacetamide (prepared by an Arbuzov reaction from triethyl phosphite and chloroacetamide), the temperature at which the mixture is subsequently stirred being increased to 50°–80° C.; instead of sodium methylate, sodium hydride suspended in DMF may advantageously be used. Melting point of the product 283°–288° C.

(b) 1. 20 ml of 10% strength sodium hydroxide solution are added to 20 g (72 millimoles) of 11-carbomethoxymethylene-5,6-dihydro-morphanthridin-6-one (compound from Example 2) in 20 ml of ethanol and the mixture is briefly heated to 60° C. and then stirred for 2 hours at room temperature. It is filtered, the filtrate is acidified with 10% strength hydrochloric acid, and the crystals which have precipitated are filtered off and thoroughly washed with water. 19.0 g (99%) of 5,6-dihydro-morphanthridin-6-one-11-methylene-carboxylic acid are obtained; melting point 273°–275° C.

2. 80 ml of thionyl chloride are added to 6.0 g (23 millimoles) of 5,6-dihydro-morphanthridin-6-one-11-methylene-carboxylic acid and the mixture is stirred at room temperature. Solution occurs within 1 hour. After stirring the mixture for a further hour, the thionyl chloride is stripped off under reduced pressure from an oil pump, the residue is taken up in a small amount of toluene and the solvent is again completely stripped off. The 5,6-dihydro-morphanthridin-6-one-11-methylene-carboxylic acid chloride which remains is sufficiently pure to be reacted further. The residue is taken up in 200 ml of concentrated ammonia, ethanol is added, whilst stirring, until all has dissolved, and the mixture is heated for 2–3 hours at 90° C. It is cooled and concentrated to ¼ of its volume, and the solids which have precipitated are filtered off. 4.8 g (79%) of 11-carboxamidomethylene-5,6-dihydro-morphanthridin-6-one are obtained; melting point 284°–288° C.

EXAMPLE 4 cis,trans-11-N-Methylcarboxamidomethylene-5,6-dihydro-morphanthridin-6-one (a) The compound is prepared by a method similar to Example 3a, using diethyl-N-methyl-phosphonoacetamide (prepared by an Arbuzov reaction from triethyl phosphite and N-methylchloroacetamide). Melting point 251°–254° C.

(b) The compound is prepared by a method similar to Example 3b: 200 ml of 40% strength aqueous methylamine solution are added to 5.0 g (18 millimoles) of 5,6-dihydro-morphanthridin-6-one-11-methylene-carboxylic acid chloride and the mixture is stirred for 2 hours at 80°–90° C. It is worked up as described above, giving 4.7 g (94%) of 11-N-methylcarboxamidomethylene-5,6-dihydro-morphanthridin-6-one; melting point 250°–253° C.

EXAMPLE 5 cis,trans-11-N,N-dimethyl-carboxamidomethylene-5,6-dihydro-morphanthridin-6-one (a) The compound is prepared by a method similar to Example 3a, using diethyl N,N-dimethyl-phosphonoacetamide (prepared by an Arbuzov reaction from triethyl phosphite and N,N-dimethylchloroacetamide). Melting point 88°–94° C.

(b) The compound is prepared by a method similar to Example 4b, using a 40% strength aqueous dimethylamine solution: 11-N,N-dimethyl-carboxamidomethylene-5,6-dihydro-morphanthridin-6-one; melting point 89°–94° C.

EXAMPLE 6 cis,trans-5,6-Dihydro-11-methylcarbonyl-methylene-morphanthridin-6-one

The compound is prepared by a method similar to Example 1a, using dimethyl 2-oxopropyl-phosphonic acid ester as the Wittig-Horner reagent. Melting point 167°–168° C.

EXAMPLE 7 cis,-trans-11-(α-Methyl)-cyanomethylene-5,6-dihydro-morphanthridin-6-one 11-(α-Methyl)-cyanomethylene-5,6-dihydro-morphanthridin-6-one is prepared by a method similar to Example 1a, by carbonyl olefination with diethyl 1-cyano-ethylphosphonate (obtainable by an Arbuzov reaction from triethyl phosphite and 2-bromo-propionitrile, or by the method of D. L. Comins et al., Synthesis (1978), 309), advantageously using sodium hydride instead of sodium ethylate, and allowing 4–6 hours at 80° C. Melting point 256°–260° C.

EXAMPLE 8 cis,trans-9-Chloro-11-cyanomethylene-5,6-dihydro-morphanthridin-6-one (a) 9-Amino-5,6-dihydro-morphanthridine-6,11-dione:

20.0 g (90 millimoles) of 2-aminoanthraquinone are introduced into a mixture of 96 ml of concentrated sulfuric acid and 32 ml of methylene chloride and dissolved at room temperature, whilst stirring. 6.8 g (105 millimoles) of sodium azide are introduced in portions, over 5 hours, into the above reaction mixture at 20° C. (using external cooling by means of a waterbath). The reaction mixture is stirred overnight at room temperature and is then cautiously poured into 3 liters of ice water. The pH of the aqueous mixture is brought to 9 with concentrated sodium hydroxide solution and the solids which have precipitated are filtered off and washed with a copious amount of water. The crude product is dried in an oven under reduced pressure at 70° C.

In order to separate the isomer mixture—which, on the evidence of the 270 MHz $^1$H—NMR spectrum contains 4 amino-isomers—the mixture is digested in 1 liter of boiling ethanol and the insoluble material (accounting for about ¼ of the total) is filtered off hot. 4.5 g (21%) of highly enriched 9-amino-5,6-dihydro-morphanthridine-6,11-dione of melting point 295°–297° C. are obtained; the pure isomer is obtained by recrystallizing from about 200 ml of a 3:1 ethanol/dimethylformamide mixture, in the presence of active charcoal. The position of the amino group follows from the X-ray structural analysis of the corresponding end product of the formula V (Example 24).

$^1$H—NMR (270 MHz, D$_6$DMSO): $\delta = 6.30$ (s, NH$_2$), 6.97 (d, 1H), 7.01 (s, 1H), 7.20 (t, 1H), 7.37 (d, 1H), 7.59 (t, 1H), 7.72 (d, 1H), 7.98 (d, 1H), 10.70 (s, NH).

The 2-, 3- and 8-amino-5,6-dihydro-morphanthridine-6,11-diones which remain in the ethanolic mother liquor can be enriched by fractional crystallization. The fractions are in each case analyzed by recording the 270 MHz $^1$H—NMR spectrum.

(b) 9-Chloro-5,6-dihydro-morphanthridine-6,11-dione:

3.0 g (12.6 millimoles) of 9-amino-5,6-dihydro-morphanthridine-6,11-dione are introduced into a mixture of 120 ml of water and 120 ml of concentrated hydrochloric acid. A solution of 0.87 g (12.6 millimoles) of sodium nitrite in 10 ml of H$_2$O is added dropwise at 0°–5° C., with thorough stirring, and stirring is then continued for 2.5 hours at the same temperature. A small amount of urea is then added to destroy the excess nitrous acid, after which 120 millimoles of a freshly prepared Cu(I) chloride catalyst in concentrated hydrochloric acid are added, resulting in evolution of nitrogen. The mixture is stirred for a further 30 minutes at room temperature and is then heated for 1 hour at 100° C., with constant stirring. After it has cooled, the reaction mixture is poured into ice water and is extracted with three $\times$ 300 ml of methylene chloride. The combined organic phases are then washed with water, dried and concentrated. 1.9 g of 9-chloro-5,6-dihydro-morphanthridine-6,11-dione are obtained; melting pont 265°–267° C.

(c) Further reaction to give the end product, by a method similar to Example 1:

cis,trans-9-Chloro-11-cyanomethylene-5,6-dihydro-morphanthridin-6-one: melting point 250°–255° C.

EXAMPLE 9 cis,trans-2-, 3-, 8- and 9-Chloro-11-cyanomethylene-5,6-dihydro-morphanthridin-6-one The monochloro-5,6-dihydro-morphanthridine-6,11-dione isomer mixture (essentially containing 3 differently chlorinated isomers), employed as the starting material and obtained by ring enlargement of 2-chloroanthraquinone, using the method of L. H. Werner et al., J. Med. Chem. 8, (1965), 74, proved impossible to separate by fractional crystallization, contrary to the statement by L. H. Werner et al., loc. cit. (It is true that fractions with similar melting points were obtained, as stated by L. H. Werner et al., loc. cit., but on the evidence of the 270 MHz $^1$H—NMR spectrum these fractions were each mixtures of 2 to 3 isomers). Hence, the further reactions were carried out with the isomer mixture and a separation was only performed on the corresponding end product of the formula V (Example 25). The carbonyl olefination (by a method similar to Example 1) gives a mixture of the 2-, 3-, 8- and 9-chloro-11-cyanomethylene-5,6-dihydromorphanthridin-6-one isomers, of melting point 148°–151° C.

EXAMPLE 10 cis,trans-4-Chloro-11-cyanomethylene-5,6-dihydro-morphanthridin-6-one

The starting material used was the ring enlargement product of 1-chloroanthraquinone, prepared by the method of L. H. Werner et al., J. Med. Chem. 8 (1965), 74; which was separated by column chromatography (silica gel, 95/5 methylene chloride/methanol), giving the polar component (thin layer of silica gel, 85/15 toluene/methanol). The 4-position of the chlorine was not separately confirmed. The Wittig reaction (Example 1) gives 4-chloro-11-cyanomethylene-5,6-dihydro-morphanthridin-6-one, of melting point 231°–233° C.

EXAMPLE 11 cis,trans-7-Chloro-11-cyanomethylene-5,6-dihydro-morphanthridin-6-one

The starting material used is the non-polar component (thin layer of silica gel, 85/15 toluene/methanol) of monochloro-5,6-dihydro-morphanthridine-6,11-dione (see Example 10), of melting point 269°–270° C.

The 7-position of the chlorine was not independently confirmed. Carbonyl olefination (by a method similar to Example 1) gives 7-chloro-11-cyanomethylene-5,6-dihydro-morphanthridin-6-one of melting point 207°–210° C.

EXAMPLE 12 cis,trans-2-Chloro-11-cyanomethylene-5,6-dihydro-morphanthridin-6-one

The starting material used is 2-chloro-5,6-dihydro-morphanthridine-6,11-dione (E. Hardtmann and H. Ott, J. Org. Chem. 34 (1969), 2244–2248).

Carbonyl olefination by a method similar to Example 1 gives 2-chloro-11-cyanomethylene-5,6-dihydro-morphanthridin-6-one, of melting point >270° C.

EXAMPLE 13 cis,trans-9-Fluoro-11-cyanomethylene-5,6-dihydro-morphanthridin-6-one (a) 3.6 g (15.1 millimoles) of 9-amino-5,6-dihydro-morphanthridine-6,11-dione (Example 8a) are suspended in a mixture of 100 ml of water and 100 ml of concentrated hydrochloric acid. After the mixture has cooled to 0°–5° C., a solution of 1.06 g (15.1 millimoles) of sodium nitrite in 20 ml of water is added dropwise, with thorough stirring. The yellow reaction mixture is then stirred for a further 2 hours at 0°–5° C. 100 ml of 50% strength tetrafluoboric acid are then added and stirring is continued for 1 hours at the same temperature.

The precipitate is filtered off and washed with a copious amount of water. After having been dried in air, the diazonium tetrafluoborate (4.8 g) is heated in a twoneck flask equipped with a reflux condenser, under a gentle stream of nitrogen. The reaction commences at about 110° C. bath temperature. When the reaction has subsided, the bath temperature is raised to 200° C. for 15 minutes. When the mixture has cooled, the solids are purified by boiling three times in methanol, using 50 ml each time, and are filtered off hot. A further amount of the product crystallizes from the methanolic mother liquors.

In total, 3.2 g of cis,trans-5,6-dihydro-9-fluoro-morphanthridine-6,11-dione, of melting point 250°–254° C., are obtained.

(b) Further reaction to give the end product, by a method similar to Example 1:
cis,trans-9-Fluoro-11-cyanomethylene-5,6-dihydro-morphanthridin-6-one: melting point 280°–285° C.

EXAMPLE 14 cis,trans-3-Methyl-11-cyanomethylene-5,6-dihydro-morphanthridin-6-one

The starting material used is the ring enlargement product of 2-methyl-anthraquinone, prepared by the method of L. H. Werner et al., J. Med. Chem. 8 (1965), 74 from which the more sparingly soluble fraction is isolated by fractional crystallization from toluene and recrystallization from dimethylformamide, giving 3-methyl-5,6-dihydro-morphantridine-6,11-dione of melting point 259°–263° C.

Carbonyl olefination (by a method similar to Example 1) gives cis,trans-3-methyl-11-cyanomethylene-5,6-dihydro-morphanthridin-6-one, of melting point 233°–235° C.

EXAMPLE 15 cis,trans-2-Methyl-11-cyanomethylene-5,6-dihydro-morphanthridin-6-one

The starting material used is 2-methyl-5,6-dihydro-morphanthridine-6,11-dione, of melting point 198°–202° C., obtained by recrystallizing the more readily toluene-soluble fraction—see Example 14—from 1:2 dioxane/ethanol.

Products enriched in one of the two residual monomers, namely 8- or 9-methyl-5,6-dihydro-morphanthridine-6,11-dione, may also be obtained by further fractional crystallization of the dioxane/ethanol mother liquor.

Carbonyl olefination gives cis,trans-2-methyl-11-cyanomethylene-5,6-dihydro-morphanthridin-6-one of melting point 228°–230° C.

EXAMPLE 16 cis,trans-2-, 3-, 8- and 9-Trifluoromethyl-11-cyanomethylene-5,6-dihydro-morphanthridin-6-one The preparation of the starting material, 2-trifluoromethylanthraquinone, is described in German Pat. No. 713,745.

The ring enlargement, to give the four isomers, namely 2-, 3-, 8- and 9-trifluoromethyl-5,6-dihydro-morphanthridine-6,11-dione, is carried out by a method similar to Example 8a. Recrystallization from toluene gives the isomer mixture, of melting point 177°–179° C. The individual isomers can be enriched by fractional crystallization from ethanol. A trifluoromethyl-5,6-dihydro-morphanthridine-6,11-dione isomer of melting point 230°–234° C. crystallizes in the highest yield.

Further conversion to the end product, by a method similar to Example 1, gives a cis,trans-2-, 3-, 8- and 9-trifluoromethyl-11-cyanomethylene-5,6-dihydro-morphanthridin-6-one isomer mixture, of melting point 130°–133° C.

II. Preparation of compounds of the general formula V:

EXAMPLE 17 cis- and trans-11-Cyanomethylene-6-(4-methyl-piperazin-1-yl)-morphanthridine (a) 160 ml of phosphorus oxychloride and 3.5 ml of N,N-dimethylaniline are added to 20.0 g (81 millimoles) of 11-cyanomethylene-5,6-dihydro-morphanthridin-6-one (cis,trans-isomer mixture) and the batch is refluxed for 4 hours under nitrogen. The excess phosphorus oxychloride and dimethylaniline are then completely distilled off under reduced pressure from an oil pump, the residue is partitioned between methylene chloride and water, the aqueous phase is extracted twice more with methylene chloride, and the combined organic phases are thoroughly washed with dilute HCl and with water, dried and evaporated, giving 20.8 g (97%) of 6-chloro-11-cyanomethylene-morphanthridine, which is sufficiently pure for further reaction.

60 ml of N-methyl-piperazine are added to 20.8 g (79 millimoles) of 6-chloro-11-cyanomethylene-morphanthridine and the mixture is stirred for 3–5 hours at 110° C. under nitrogen. When it has cooled, the dark homogeneous reaction mixture is poured into ice water and the yellowish crude product, consisting of 11-cyanomethylene-6-(4-methyl-piperazin-1-yl)-morphanthridine, is filtered off, dried in an oven under reduced pressure and recrystallized from ethanol in the presence of active charcoal. 19.5 g (75%) of yellow 11-cyanomethylene-6-(4-methyl-piperazin-1-yl)-morphanthridine are obtained in the form of a cis,trans-isomer mixture, of melting point 148°–150° C.

To separate the cis- and trans-isomers, the isomer mixture is digested in about 80 ml of boiling methanol and the insoluble material is filtered off hot. This gives 3.1 g of a yellow solid which on the evidence of the thin layer chromatogram (silica gel, 85/15 toluene/methanol as the migrating agent) consists in the main of the non-polar isomer a. The filtrate is concentrated and the residue is taken up in a small amount of boiling methylene chloride, only just sufficient to dissolve all the material. On cooling, 3.0 g of a yellow product crystallize out; this is filtered off rapidly and washed with a very small amount of ice-cold methylene chloride. Thin layer chromatography indicates a very good degree of enrichment in polar isomer b.

By repeating these two successive operations several times, about 10–11 g fractions of each of the highly enriched isomers, coded a and b, are obtained, and these are then recrystallized once or twice more from ethanol.

Pure isomer a is obtained in the form of yellow rectangular flakes of melting point 210°–212° C., and pure isomer b in the form of yellow sharp needles of melting point 182°–184° C.

X-ray structural analysis indicates that a is the cis-isomer and b the trans-isomer of 11-cyanomethylene-6-(4-methyl-piperazin-1-yl)-morphanthridine.

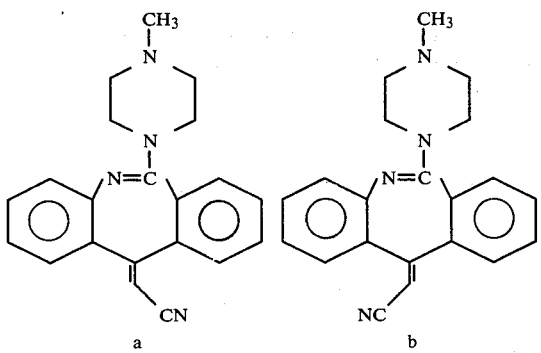

a     b

EXAMPLE 18 cis,trans-11-Carbomethoxymethylene-6-(4-methyl-piperazin-1-yl)-morphanthridine

The compound is prepared by a method similar to Example 17 from 11-carbomethoxymethylene-5,6-dihydromorphanthridin-6-one (obtained in Example 2): the crude product is purified by column chromatography over silica gel, with methylene chloride as migrating agent. The cis,trans-isomer mixture is obtained in 45% yield, as yellow crystals of melting point 75°–79° C.

EXAMPLE 19 cis,trans-11-Carboxamidomethylene-6-(4-methyl-piperazin-1-yl)-morphanthridine

The compound is prepared by a method similar to Example 17, from 11-carboxamidomethylene-5,6-dihydromorphanthridin-6-one (obtained in Example 3): after recrystallization from ethanol, a 65% yield of cis,transisomer mixture is obtained in the form of yellow crystals of melting point 185°–193° C.

EXAMPLE 20 cis,trans-11-N-Methyl-carboxamidomethylene-6-(4-methylpiperazin-1-yl)-morphanthridine The compound is prepared by a method similar to Example 17, from 11-N-methylcarboxamidomethylene-5,6-dihydro-morphanthridin-6-one (obtained in Example 4): the cis,trans-11-N-methyl-carboxamidomethylene-6-(4-methyl-piperazin-1-yl)-morphanthridine is purified by column chromatography over silica gel, using 95/5 methylene chloride/methanol as the migrating agent. This gives yellow crystals of melting point 118°–124° C.

EXAMPLE 21 cis,trans-11-N,N-Dimethyl-carboxamidomethylene-6-(4-methyl-piperazin-1-yl)-morphanthridine.$H_2O$ The compound is prepared by a method similar to Example 20, from 11-N,N-dimethyl-carboxamidomethylene-5,6-dihydro-morphanthridin-6-one (obtained in Example 5): yellow crystals, of melting point 161°–163° C.

EXAMPLE 22 cis,trans-11-Methylcarbonyl-methylene-6-(4-methyl-piperazin-1-yl)-morphanthridine.$H_2O$ The compound is prepared by a method similar to Example 20, from 5,6-dihydro-11-methylcarbonyl-methylene-morphanthridin-6-one (obtained in Example 6): yellow crystals, of melting point 133°–136° C.

EXAMPLE 23 cis,trans-11-(α-Methyl)-cyanomethylene-6-(4-methyl-piperazin-1-yl)-morphanthridine.$\frac{1}{2}H_2O$.

The compound is prepared by a method similar to Example 17, from 11-(α-methyl)-cyanomethylene-5,6-dihydro-morphanthridin-6-one (obtained in Example 7): after purification by column chromatography over silica gel, using 95/5 methylene chloride/methanol, yellow crystals of melting point 96°–98° C. are obtained.

EXAMPLE 24 cis,trans-9-Chloro-11-cyanomethylene-6-(4-methyl-piperazin-1-yl)-morphanthridine The compound is prepared by a method similar to Example 17, from 9-chloro-11-cyanomethylene-5,6-dihydromorphanthridin-6-one (obtained in Example 9): melting point 90°–95° C.

To separate the cis- and trans-isomers, the mixture is subjected to fractional recrystallization from ethanol. The pure cis-isomer (non-polar component on a thin layer silica gel plate, using 85/15 toluene/methanol as the migrating agent), being the more sparingly soluble fraction, crystallizes out first; melting point 173°–174° C.

X-ray structural analysis confirms the 9-position of the chlorine in the cis-isomer.

EXAMPLE 25 cis,trans-3- and 8-Chloro-11-cyanomethylene-6-(4-methylpiperazin-1-yl)-morphanthridine.

The compound is prepared by a method similar to Example 17, from the monochloro-11-cyanomethylene-5,6-dihydro-morphanthridin-6-one isomer mixture obtained in Example 9: the end product, consisting of 8 isomers (as indicated by thin layer chromatography on silica gel, using 85/15 toluene/methanol; doubling due to cis,trans-isomerism), and having a melting point of 95°–99° C., is recrystallized from ethanol and then subjected to column chromatography (silica gel, 95/5 methylene chloride/methanol) to produce enrichment of the individual fractions. This allows isolation, and characterization, of the cis,trans-2- and -9-chloro-11-cyanomethylene-6-(4-methyl-piperazin-1-yl)-morphanthridine isomers, described in Examples 28 and 24, and constituting the polar and less polar constituents respectively.

The remaining cis,trans-3- and -8-chloro-11-cyanomethylene-6-(4-methyl-piperazin-1-yl)-morphanthridine isomers, which still remain, are obtained in an enriched form as further fractions. Yellow crystals of melting point 95°–98° C.

EXAMPLE 26 cis,trans-4-Chloro-11-cyanomethylene-6-(4-methylpiperazin-1-yl)-morphanthridine.$\frac{1}{2}H_2O$ The compound is prepared by a method similar to Example 17, from 4-chloro-11-cyanomethylene-5,6-dihydromorphanthridin-6-one (obtained in Example 10): column chromatography (silica gel, using 95/5 methylene chloride/methanol) gives yellow crystals of melting point 90°–95° C.

EXAMPLE 27 cis,trans-7-Chloro-11-cyanomethylene-6-(4-methylpiperazin-1-yl)-morphanthridine

The compound is prepared by a method similar to Example 17, from 7-chloro-11-cyanomethylene-5,6-dihydromorphanthridin-6-one (obtained in Example 11): yellow crystals of melting point 219°–221° C.

EXAMPLE 28 cis,trans-2-Chloro-11-cyanomethylene-6-(4-methylpiperazin-1-yl)-morphanthridine.½H$_2$O The compound is prepared by a method similar to Example 17, from 2-chloro-11-cyanomethylene-5,6-dihydromorphanthridin-6-one (obtained in Example 12): yellow crystals of melting point 157°–162° C.

EXAMPLE 29 cis,trans-9-Fluoro-11-cyanomethylene-6-(4-methylpiperazin-1-yl)-morphanthridine

The compound is prepared by a method similar to Example 17, from 9-fluoro-11-cyanomethylene-5,6-dihydromorphanthridin-6-one (obtained in Example 13): melting point 120°–125° C.

EXAMPLE 30 cis,trans-3-Methyl-11-cyanomethylene-6-(4-methylpiperazin-1-yl)-morphanthridine

The compound is prepared by a method similar to Example 17, from 3-methyl-11-cyanomethylene-5,6-dihydromorphanthridin-6-one (obtained in Example 14): yellow crystals of melting point 192°–200° C. The 3-position of the methyl group is established by X-ray structural analysis.

To separate the cis- and trans-isomers, the isomer mixture is subjected to fractional recrystallization from methanol. The first fraction obtained (thin layer of silica gel, 85/15 toluene/methanol) is highly enriched non-polar isomer, which is again recrystallized from methanol. X-ray structural analysis shows that this isomer, of melting point 224° C., is cis-3-methyl-11-cyanomethylene-6-(4-methyl-piperazin-1-yl)-morphanthridine.

The corresponding polar trans-isomer is best obtained by fractionally crystallizing the residue from the mother liquor, obtained above, from cyclohexane; the pure trans-3-methyl-11-cyanomethylene-6-(4-methylpiperazin-1-yl)-morphanthridine melts at 193°–195° C.

EXAMPLE 31 cis,trans-2-Methyl-11-cyanomethylene-6-(4-methylpiperazin-1-yl)-morphanthridine

The compound is prepared by a method similar to Example 17, from 2-methyl-11-cyanomethylene-5,6-dihydromorphanthridin-6-one (obtained in Example 15): yellow crystals of melting point 162°–164° C. The 2-position of the methyl group is established by X-ray structural analysis.

To separate the cis- and trans-isomers, the isomer mixture is subjected to fractional recrystallization from ethanol. The first fraction obtained (thin layer of silica gel, 85/15 toluene/methanol) is highly enriched polar isomer, which is again recrystallized from ethanol. X-ray structural analysis shows that this isomer of melting point 183° C., is trans-2-methyl-11-cyanomethylene-6-(4-methyl-piperazin-1-yl)-morphanthridine.½H$_2$O.

The corresponding non-polar cis-isomer is best obtained by repeated column chromatography (silica gel, 98/2 methylene chloride/methanol as the migrating agent) of the residue of the mother liquors, obtained above, of melting point 92°–95° C.

EXAMPLE 32 cis,trans-2-, 3-, 8- and 9-Trifluoromethyl-11-cyanomethylene-6-(4-methyl-piperazin-1-yl)-morphanthridine.½H$_2$O The compound is prepared by a method similar to Example 17, from 2-, 3-, 8- and 9-trifluoromethyl-11-cyanomethylene-5,6-dihydro-morphanthridin-6-one (obtained in Example 16): melting point 93°–96° C.

EXAMPLE 33

General procedure for the preparation of the end products of the general formula V by introducing the various nucleophilic alkylamino or alkoxy radicals A into the 6-position of the 6-chloro-morphanthridine derivatives IV.

The 6-chloro-morphanthridine derivative is mixed with from 2 to 5 equivalents of the alkylamine or aminoalkanol AH and the mixture is heated at 110° C. under nitrogen for from 3 to 5 hours. Where the nucleophilic agent AH is volatile, the excess thereof is then distilled off under reduced pressure. In such cases, the residue is then taken up in ice water and repeatedly extracted with methylene chloride; where the nucleophilic agent is not volatile, the entire reaction mixture is taken up in ice water and extracted repeatedly with methylene chloride. The combined methylene chloride phases are then washed with water, dried and concentrated. The crude product which remains is either recrystallized from ethanol in the presence of active charcoal or (especially where alkylamines of relatively high molecular weight are present) is purified by column chromatography over silica gel, using 95/5 methylene chloride/methanol.

The following are examples of compounds of the formula V prepared by the above general method:

34. cis,trans-11-Cyanomethylene-6-(4-β-hydroxyethylpiperazin-1-yl)-morphanthridine.½H$_2$O, melting point 111°–113° C.

35. cis,trans-11-Cyanomethylene-6-piperazin-1-yl-morphanthridine.H$_2$O, melting point 208°–211° C.

36. cis,trans-11-Cyanomethylene-6-(4-ethyl-piperazin-1-yl)-morphanthridine, melting point 86°–90° C.

Separation of the cis- and trans-11-cyanomethylene-6-(4-ethyl-piperazin-1-yl)-morphanthridine isomers: to separate the cis- and trans-isomers, the isomer mixture is subjected to fractional recrystallization from methanol. The less soluble fraction, which crystallizes out first, is the trans-isomer (the polar component on a silica gel thin layer plate, using 85/15 toluene/methanol as the migrating agent). Recrystallization from ethanol gives the pure trans-isomer, of melting point 181°–183° C.

Column chromatography over silica gel, using 95/5 methylene chloride/methanol, gives the less polar cis-isomer in a purified form, of melting point 138°–140° C.

37. cis,trans-11-Cyanomethylene-6-homopiperazin-1-yl-morphanthridine.HCl.H$_2$O, melting point 175°–178° C.

38. cis,trans-11-Cyanomethylene-6-(2-dimethylaminoethylamino)-morphanthridine.½H$_2$O, melting point 76°–79° C.

39. cis,trans-11-Cyanomethylene-6-(2-piperidin-1-ylethylamino)-morphanthridine.½H₂O, melting point 83°–85° C.

Separation of the cis- and trans-11-cyanomethylene-6-(2-piperidin-1-yl-ethylamino)-morphanthridine isomers: the cis- and trans-isomers can be separated by column chromatography over silica gel, using 95/5 methylene chloride/methanol. The cis-isomer (the non-polar component on a silica gel thin layer plate, using 85/15 toluene/methanol as the migrating agent) is obtained in the form of yellow crystals of melting point 76°–78° C., whilst the more polar trans-isomer melts at 103°–106° C.

40. cis,trans-11-Cyanomethylene-6-(N'-methyl-homopiperazin-1-yl)-morphanthridine.0.75 H₂O, melting point 73°–80° C.

41. cis,trans-11-Cyanomethylene-6-(N-methyl-piperidin-3-yl-methoxy)-morphanthridine.H₂O, melting point 93°–95° C.

42. cis,trans-11-Cyanomethylene-6-(N-methyl-piperidin-2-yl-methoxy)-morphanthridine, melting point 67°–70° C.

43. cis,trans-11-Cyanomethylene-6-(N-methyl-piperidin-3-yl-methylamino)-morphanthridine.H₂O, melting point 110°–114° C.

EXAMPLE 44 cis,trans-11-Cyanomethylene-6-(4-methyl-4-oxy-piperazin-1-yl)-morphanthridine.2H₂O 3.0 g (9.1 millimoles) of cis,trans-11-cyanomethylene-6-(4-methyl-piperazin-1-yl)-morphanthridine are dissolved in 100 ml of hot ethanol and 1.5 ml of 30% strength hydrogen peroxide are added. The mixture is refluxed for 5 hours, and the excess hydrogen peroxide is then destroyed by dropping a small sheet of platinum into the reaction mixture and refluxing for a further 2 hours. The reaction mixture is then filtered, the filtrate is evaporated and the resulting N-oxide is purified by column chromatography over silica gel, using 95/5 methylene chloride/methanol as the migrating agent. 2.5 g (80%) of yellow crystals of melting point 141°–148° C. are obtained.

To separate the cis- and trans-isomers, the isomer mixture is subjected to fractional recrystallization from a small amount of methylene chloride. The first fraction isolated is highly enriched non-polar isomer (according to a thin layer chromatogram on silica gel, using 85/15 toluene/methanol), and is recrystallized from a small amount of ethanol. By analogy to the cis,trans-isomer analyses described above, this isomer, of melting point 241° C., is taken to belong to the cis-series.

The corresponding polar trans-isomer, of melting point 169° C., is obtained by column chromatography over silica gel, using 95/5 methylene chloride/methanol as the migrating agent, of the residue of the mother liquor, obtained above.

Advantageously, both isomers are prepared directly by oxidizing, respectively, the cis- and trans-11-cyanomethylene-6-(4-methyl-piperazin-1-yl)-morphanthridines (prepared, and separated, as described in Example 17) by the method described above; no cis,trans-isomerization occurs during the oxidation.

According to the results of pharmacological experiments, the compounds of the formula V possess sedative, apomorphine-antagonistic, analgesic, reserpineantagonistic or anti-cholinergic effects and may therefore be used as neuroleptics, sedatives, hypnotics, analgesics, anti-depressants or agents for counteracting Parkinson's syndrome.

The following methods were used to analyze the effects of the compounds:

1. Sedative effect

The substances are administered orally to groups of 4×3 or 8×3 female NMRI mice. The orientation hypermotility induced by a new environment is determined photoelectrically, 30 minutes after the administration of the substances, for a period of 30 minutes. The ED 50% is taken as the dose which reduces the orientation hypermotility by 50%, compared to untreated control animals.

2. Analgesic effect

The analgesic effect is determined by means of the D'amour and Smith (1941) tail-flick method. In this, the substances are administered intraperitoneally to groups of 10 female NMRI mice. The pain reaction is triggered 30 minutes after administration. The reaction time, until the tail is flicked out of the way after exposure to a focused light beam, is measured.

The ED 100% is the dose which lengthens the reaction time by 100% compared to a control group.

3. Anti-cholinergic effect

A lethal dose (0.825 mg/kg) of Physostigmin is administered subcutaneously to groups of 10 female NMRI mice. The test substances are administered orally 30 minutes before administering the Physostigmin.

The ED 50% is the dose of substance which protects 50% of the animals against death from Physostigmin.

4. Apomorphine-antagonistic effect

Jaw motions are triggered in groups of 4–6 female Sprague-Dawley rats by subcutaneous administration of 1.5 mg of apomorphine/kg, and are recorded by means of implanted electrodes (KUBACKI mandibulogram, 1978).

The ED 50% is the dose which reduces the number of jaw movements by 50% compared to untreated control animals.

5. Acute toxicity

The substances are administered intraperitoneally to groups of 5–10 female NMRI mice. The LD 50 is the dose which causes the death of 50% of the treated animals.

In these Experiments (Table 1) strong sedative effects are observed with the compounds of Example 17 (cis-trans mixture and cis-isomer), Example 30 (cis-trans mixture and cis-isomer), Example 31 (cis-trans mixture), Example 36 (cis-trans mixture) and Example 39 (cis-trans mixture), which are of the order of magnitude of the effects of the reference substances Clozapin or Perlapin, or even exceed these.

An analgesic effect is found with the compound of Example 30 (cis-trans mixture and cis-isomer). The cis-isomer is substantially more active than Clozapin.

The anti-cholinergic effect observed from the Physostigmin antagonism manifests itself especially in the case of the compounds of Example 17 (cis-trans mixture and trans-isomer), Example 31 (cis-trans mixture), Example 36 (cis-trans mixture and trans-isomer), Example 37 (cis-trans mixture) and Example 44 (cis-trans mixture and trans-isomer). In the case of Example 17 (cis-trans mixture), Example 31 (cis-trans mixture) and Example 36 (cis-trans mixture) it is found to be accompanied by relatively strong sedative effects (see above), similarly to the behavior of Clozapin.

Together with the above effects, most of the compounds also show an apomorphine-antagonistic effect which is typical of neuroleptics and which is also shown by the reference substances. If the pharmacological properties of the cis-trans-isomer mixtures concerned are compared with those of the individual pure isomers, it is found, surprisingly, that there are not only quantitative but also qualitative differences so that novel and interesting combinations of effects are found for various substances.

stronger anti-cholinergic and apomorphine-antagonistic effect, and, as in the case of the trans-isomer of Example 17, differ, in their effects, from the corresponding isomer mixtures.

Another isomer mixture, namely that of Example 30, has a high sedative activity (greater than that of Clozapin and Perlapin) with a moderate anti-cholinergic effect and a stronger analgesic effect. The cis-isomer is responsible for the strong sedative and strong analgesic effects. This compound, exhibiting a combination of sedative plus analgesic effect, with no anti-cholinergic effect and a weaker apomorphine-antagonistic effect than that of Clozapin and Perlapin, again offers a novel type of effect.

TABLE

| Compound No. | Geometrical isomerism | Sedative effect ED 50% | Sedative effect R.A.[1] | Analgesic effect ED 100% | Analgesic effect R.A. | Apomorphine antagonfam ED 50% | Apomorphine antagonfam R.A. | Anti-cholinergic effect ED 50% | Anti-cholinergic effect R.A. | Toxicity LD 50 |
|---|---|---|---|---|---|---|---|---|---|---|
| 17 | cis-trans M[2] | 2.78 | 1.71 | 46.4 | 0.04 | 22 | 0.37 | 6.26 | 2.25 | 121 |
|  | cis-isomer | 1.98 | 2.39 | 31.6 | 0.07 | 46 | 0.17 | 17.4 | 0.81 | 147 |
|  | trans-isomer | >21.5 | <0.22 | >21.5 | <0.10 | 12 | 0.67 | 4.7 | 3.00 | 332 |
| 30 | cis-trans M | 0.804 | 5.90 | 5.17 | 0.40 | 35 | 0.23 | 31.2 | 0.45 | 178 |
|  | cis-isomer | 1.06 | 4.47 | 0.740 | 2.18 | 85 | 0.09 | 100 | 0.14 | 287 |
|  | trans-isomer | 33.6 | 0.14 | 68.1 | 0.03 | 19 | 0.42 | 12.3 | 1.15 | >100 |
| 31 | cis-trans M | 3.35 | 1.41 | 10.0 | 0.21 | 42 | 0.19 | 2.74 | 5.15 | 50.0 |
| 36 | cis-trans M | 3.34 | 1.42 | >10.0 | <0.21 | 43 | 0.19 | 7.80 | 1.81 | 100 |
|  | trans-isomer | >100 | >0.04 | >46.4 | <0.04 | 22 | 0.37 | 5.60 | 2.52 | >100 |
| 37 | cis-trans M | >21.5 | >0.22 | 46.4 | 0.04 | >100 | <0.08 | 5.49 | 2.57 | 69.8 |
| 39 | cis-trans M | 1.61 | 2.94 | >10.0 | >0.21 | 46 | 0.17 | >10.0 | >1.41 | 5.35 |
| 44 | cis-trans m | 14.3 | 0.33 | >46.4 | <0.04 | 85 | 0.09 | 1.98 | 7.12 | 464 |
|  | cis-isomer | 17.6 | 0.26 | >46.4 | <0.04 | >100 | <0.08 | 100 | 0.14 | 261 |
|  | trans-isomer | 100 | 0.04 | >100 | <0.02 | 25 | 0.32 | 3.74 | 3.77 | 559 |
| Clozapin → |  | 4.74 | 1.00 | 2.08 | 1.00 | 8 | 1.00 | 14.1 | 1.00 | 215 |
| Perlopin → |  | 2.05 | 2.31 | >21.5 | <0.10 | 22 | 0.37 | >21.5 | <0.66 | 215 |

[1]R.A. = relative activity
[2]M = mixture

The pattern of effects exhibited by the cis-trans mixture from Example 17 resembles that of the reference substance Clozapin. However, the mixture is more strongly sedative and anti-cholinergic and is not analgesically active. The apomorphine-antagonistic effect is somewhat weaker than that of Clozapin.

The cis-isomer of the compound of Example 17 is responsible for the sedative effect, and shows, relative to Clozapin, an approximately comparable anti-cholinergic effect and a lower apomorphine-antagonistic effect.

The trans-isomer of the compound of Example 17, on the other hand, particularly exhibits an anti-cholinergic and apomorphine-antagonistic effect. The sedative effect is very slight. This type of effect is novel and is clearly different from that of Clozapin and of Perlapin.

The trans-isomers of the compounds of Examples 30, 36 and 44 also have little or no sedative effect but a

We claim:
1. A compound of formula I

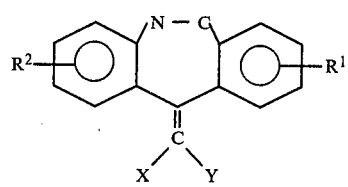

where $R^1$ and $R^2$ are hydrogen, chlorine or methyl, X is hydrogen or methyl and Y is methylcarbonyl.

2. cis,trans-5,6-Dihydro-11-methylcarbonyl-methylenemorphanthridin-6-one.

* * * * *